United States Patent [19]

Knöfel et al.

[11] Patent Number: 4,914,236

[45] Date of Patent: Apr. 3, 1990

[54] PROCESS FOR THE PREPARATION OF MULTINUCLEAR AROMATIC POLYAMINES

[75] Inventors: Hartmut Knöfel, Odenthal; Michael Brockelt, Bergisch Gladbach; Marcel Petinaux; Rudolf Uchdorf, both of Krefeld, all of Fed. Rep. of Germany

[73] Assignee: Bayer Aktiengesellschaft, Bayerwerk, Fed. Rep. of Germany

[21] Appl. No.: 185,762

[22] Filed: Apr. 25, 1988

[30] Foreign Application Priority Data

May 1, 1987 [DE] Fed. Rep. of Germany ....... 3714606

[51] Int. Cl.$^4$ .................... C07C 87/50; C09B 11/02
[52] U.S. Cl. .................................................. 564/334
[58] Field of Search ........................................ 564/333

[56] References Cited

U.S. PATENT DOCUMENTS

| | | | |
|---|---|---|---|
| 3,952,042 | 4/1976 | Knofel | 260/453 |
| 3,996,283 | 12/1976 | Knofel | 260/570 |
| 4,061,678 | 12/1977 | Knofel et al. | 260/570 |
| 4,087,459 | 5/1978 | Knofel et al. | 260/570 |
| 4,093,658 | 6/1978 | Knofel et al. | 260/570 |

FOREIGN PATENT DOCUMENTS 2343658 3/1975 Fed. Rep. of Germany ...... 564/333

*Primary Examiner*—Dale R. Ore
*Attorney, Agent, or Firm*—Joseph C. Gil

[57] ABSTRACT

The present invention relates to an improved process for the preparation of multinuclear aromatic polyamines by the condensation of aniline with formaldehyde in the presence of water and acid catalysts and working up of the reaction mixture by extraction with a hydrophobic solvent. The acid catalyst obtained in the aqueous phase of extraction is reused.

9 Claims, 1 Drawing Sheet

PROCESS FOR THE PREPARATION OF MULTINUCLEAR AROMATIC POLYAMINES

BACKGROUND OF THE INVENTION

The present invention relates to an improved process for the preparation of multinuclear aromatic polyamines by the condensation of aniline with formaldehyde in the presence of water and acid catalysts and working up of the reaction mixture by extraction with a hydrophobic solvent. The acid catalyst obtained in the aqueous phase of extraction is reused.

It is already known that in the preparation of multinuclear aromatic polyamines by the condensation of aniline with formaldehyde in the presence of water and acid catalysts, the aqueous reaction mixture obtained may be worked up by extraction with a hydrophobic solvent and the acid catalyst obtained in the aqueous phase in the process of extraction may be reused (see e.g., U.S. Pat. Nos. 3,996,283; 3,952,042, 4,061,678, 4,093,658, and 4,087,459: and German Offenlegungsschrift No. 2,343,658).

The important advantage of the processes described in these prior publications is that the catalyst need not be neutralized since it is obtained in the aqueous phase when the acid reaction mixture is worked up by extraction and may be returned to the beginning of the process in this form and reused. Furthermore, certain variations of this known principle, such as those described in U.S. Pat. Nos. 4,093,658 and 4,087,459, for example, provide for the controlled production of polyamine mixtures containing a selectively increased or reduced proportion of 2,4'-isomers. The products of the processes of the prior publications are otherwise similar in their suitability as preliminary products for the preparation of polyisocyanates to conventional polyamines of the diphenyl methane series which have been prepared with neutralization of the acid catalyst used. This means that the properties of polyurethane foams prepared from such polyisocyanate mixtures of the diphenyl methane series are qualitatively approximately the same in both cases. The processes of the above mentioned prior publications have the disadvantage that extraction requires very considerable quantities of hydrophobic solvents, based on the quantity of extracted product obtained (the concentration of product of the process in the organic phases is generally below 15% by weight), which of course entails considerable expenditure for distillation and hence a high consumption of energy for working up the organic phases by distillation.

It was an object of the present invention to provide a new, improved process for the preparation of multinuclear aromatic polyamines from aniline and formaldehyde in the presence of acid catalysts which would combine the advantages of the known art processes and would in addition enable qualitatively improved products to be obtained with less expenditure of effort for distillation and hence less energy consumption.

DESCRIPTION OF THE INVENTION

Figure 1:
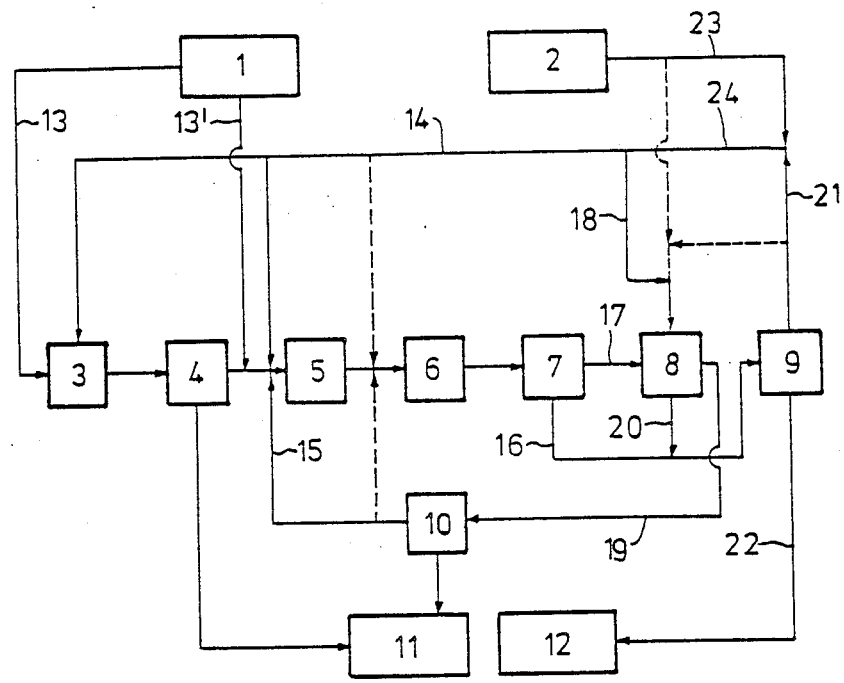
FIGS. 1 and 2 schematically set forth various embodiments of the present invention.

The above problem could be solved by the process according to the invention described below, which has the following advantages:

the acid catalyst put into the process is reused as in the known art processes and is not destroyed by neutralization:

polyamines of the diphenyl methane series (MDA) containing an increased proportion of diamines and as well as those containing a reduced proportion of diamines may be prepared by the process; polyamine mixtures containing an increased proportion of 2,4'-diamino-diphenyl methane in the dinuclear moiety, may be prepared by the process according to the invention, and the proportion of unwanted 2,2'-diamino-diphenyl methane may always be kept low even when the proportion of 2,4'-diamino-diphenyl methane is high;

the polyisocyanates prepared from the products of the process give rise to polyurethane foams which are surprisingly found to have distinctly less intrinsic coloration compared with similar polyurethane foams based on known polyisocyanate mixtures of the diphenyl methane series;

compared with the above mentioned "extraction process" known in the art, the total quantity of solvents used in the process according to the present invention may be substantially reduced so that the MDA concentration in the organic phases obtained may be considerably increased and the energy required for distillation when working up the organic phases may be correspondingly reduce.

The present invention relates to a process for the preparation of multinuclear aromatic polyamines by the reaction of aniline with formaldehyde in the presence of water and acid catalysts in a single stage or two stage reaction within the temperature range of from 0° to 180° C., optionally preceded by an aminal preliminary stage in which N,N'-disubstituted aminal is formed in the absence of acid catalyst, this disubstituted aminal being then converted into the desired end product in one or more stages in the presence of acid catalyst within the temperature range of from 0° to 180° C. The resulting reaction mixture is then worked up by extraction with a hydrophobic solvent containing aniline. The resulting organic phase is separated by distillation into (i) a distillate containing aniline-containing solvent which is used again for extraction, optionally after the addition of fresh aniline, and (ii) a distillation residue consisting substantially of end product of the process. The aqueous phase obtained from the process of extraction and containing the acid catalyst is returned and the catalyst contained therein is reused. The water of condensation produced in the process of condensation and the water introduced into the system with the aqueous solution of formaldehyde is removed in a water separator downstream of the aminal preliminary stage and upstream of the first reaction stage and/or in an evaporator downstream of the extraction stage and upstream of the first reaction stage. The process is further characterized in that (a) the formaldehyde used in the form of an aqueous solution is reacted with an aniline-containing hydrophobic solvent in an aminal preliminary stage and/or with an aniline-containing hydrophobic solvent and the recycled aqueous phase containing the catalyst in the form of amine salts in the first reaction stage by mixing the components, (b) after termination of the reaction, the resulting diphasic reaction mixture is separated into an aqueous phase and an organic phase in a phase separator upstream of the extraction stage, (c) the organic phase obtained in the phase separator is separated by distillation, either alone or together with the organic phase leaving the extraction stage, into (i) a distillate consisting of aniline-containing solvent or two distillates consisting of aniline-containing solvents and (ii) one or two distillation residues consisting substantially of end product of the process, and (d) two partial streams are prepared from the distillate (or distillates) according to (c) which two partial streams may be identical with the two distillates according to (c), one of the partial streams is mixed with the aqueous formaldehyde in the aminal preliminary stage or, in the absence of an aminal preliminary stage, it is mixed in the first reaction stage with the aqueous formaldehyde and the aqueous phase containing the acid catalyst, and the other partial stream is put into the extraction stage for extraction of the end product of the process from the aqueous phase of the reaction mixture.

More particularly, the present invention is directed to a process for the preparation of multinuclear aromatic polyamines comprising:

(A) reacting aniline and formaldehyde in the presence of water, hydrophobic solvent and acid catalysts in one or more stages, to produce a two-phase condensation mixture containing said aromatic polyamines, (B) separating said condensation mixture into an aqueous phase and an organic phase, (C) extracting said aqueous phase with a hydrophobic solvent containing aniline to produce a solvent phase and a second aqueous phase which contains the acid catalyst, (D) subjecting said organic phase and said solvent phase to distillation to produce
  (i) a distillate containing said hydrophobic solvent and aniline, and
  (ii) a distillation residue which contains said aromatic polyamines, (E) returning a portion of said distillate to step (A), (F) returning the remaining portion of said distillate to step (C), and (G) returning said second aqueous phase to step (A).

In a preferred embodiment, step (A) of the process of the present invention comprises (A)(i) condensing aniline with formaldehyde in the presence of a hydrophobic solvent and in the absence of an acid catalyst to produce a precondensate mixture containing the corresponding N,N'-disubstituted aminals, (A)(ii) removing substantially all the water from said precondensate mixture, (A)(iii) mixing the resultant water-free mixture with an aqueous solution containing acid catalyst to produce a two-phase mixture, and (A)(iv) subjecting said two-phase mixture to a rearrangement reaction in one or more stages thereby producing an aqueous condensation mixture containing said aromatic polyamines.

In this particular embodiment, step (E) can comprise returning a portion of the distillate to step (A)(i), while step (G) can comprise returning said second aqueous phase to step (A)(iii). Step (D) can comprise in either separately distilling the organic phase or the solvent phase or in first combining the two phases and thereafter subjecting the resultant mixture to distillation.

The starting materials used for the process according to the invention are aniline and formaldehyde. The formaldehyde is preferably used in the form of an aqueous solution containing from 20 to 50% by weight of formaldehyde.

The hydrophobic solvents used for the process are inert solvents boiling in the range of from 30°–250° C., preferably from 80°–200° C., such as, for example, chlorobenzene, dichlorobenzenes, benzene, toluene, xylene, dichloroethane, chloroform or carbon tetrachloride. Xylenes are preferably used as hydrophobic solvents, i.e., commercial xylene mixtures, in particular o-xylene.

The acid catalyst consists of water soluble acids having a pKa value below 2.5, preferably below 1.5. Examples include hydrochloric acid, hydrobromic acid, sulphuric acid, trifluroacetic acid, methane sulphonic acid or phosphoric acid. Hydrochloric acid is the preferred catalyst. The above mentioned acids may also be used as mixtures with acid or neutral salts of such acids, e.g. the corresponding ammonium salts or the corresponding alkali metal salts but the use of such salts is less preferred. The above mentioned acids are present in the circulating system according to the invention in the form of the corresponding ammonium salts of the circulating bases.

The process according to the invention may be carried out either in a single stage or in two stages and either with or without a preliminary aminal stage. If the process is carried out as a single stage reaction it should always be preceded by a preliminary aminal stage. By "single stage reaction process" is meant a process variation in which the aminal, after addition of the acid catalyst, is heated to a temperature of from 60°–180° C., preferably from 80°–150° C., within a short space of time, less than 10 minutes and preferably less than 5 minutes, to be rearranged into the end product, or a variation in which the aminal is directly mixed with the aqueous catalyst phase which has been heated to an elevated temperature in the region of 60°–180° C., preferably 80°–150° C. and is circulating in the system, and the mixture is then optionally heated to the desired final temperature. By "two stage reaction process" is meant an embodiment of the process in which the aminal, after addition of the acid catalyst, or the reaction mixture of aniline, formaldehyde and acid catalyst, is heated in a first reaction stage to a temperature of from 0°–60° C., preferably from 30° to 60° C., for a period of from 10 to 90 minutes, preferably from 30 to 60 minutes, and the temperature is then maintained at from 60° to 180° C., preferably from 60° to 150° C., especially from 100° to 150° C., in a second reaction stage for a period of from 30 to 180 minutes, preferably from 60 to 120 minutes. In this preferred process variation of a two stage reaction, the first reaction stage consists mainly of a rearrangement of the aminal or a condensation of the starting materials to N-benzyl aniline, which is then rearranged to the nuclear-substituted end product in the second reaction stage at an elevated temperature. According to one particular embodiment of the two stage reaction process, without or, preferably, with a preliminary aminal stage, the first reaction stage is carried out with only a partial stream of the aqueous catalyst phase, generally less than 50%, preferably less than 15% thereof. After termination of the first reaction stage and before termination of the second reaction stage, the reaction is completed in the presence of the whole catalyst phase. This embodiment is particularly suitable for the obtaining of end products containing an increased proportion of ortho isomers, in particular 2,4'-diamino diphenyl methane, with a relatively small proportion of 2,2'-isomers. The process may be carried out either continuously or batchwise. For the continuous process, the times given refer to the average dwell times of the reaction mixture in the individual stages. If the reaction stages are preceded by an aminal preliminary stage, the (average) dwell time of the starting materials at this stage is generally from 10 to 60 minutes. preferably from 15 to 40 minutes. The temperature in the aminal preliminary stage is generally from 0° to 60° C., preferably from 20° to 40° C. All stages of the process preferably take place at the intrinsic pressure of the system and preferably in an inert gas atmosphere (nitrogen).

Figure 2:
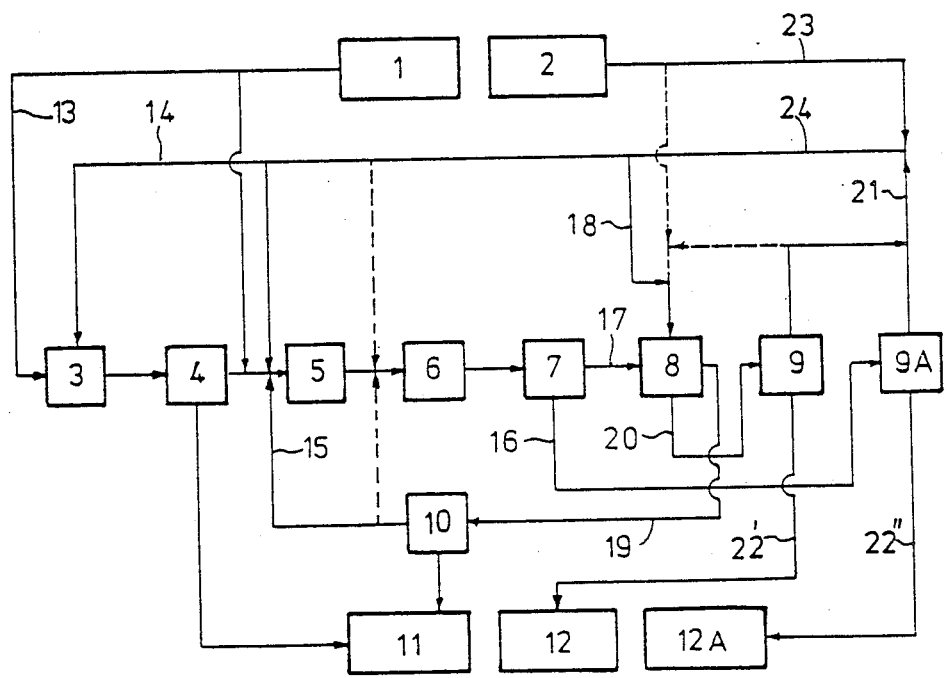

The flow diagrams of FIGS. 1 and 2 serve to illustrate the process according to the invention. The reference numerals in these figures have the following meanings:

(1) a tank for aqueous formaldehyde solution
(2) a tank for aniline
(3) a condensation reactor (aminal preliminary stage)
(4) a water separator
(5) the first reaction stage
(6) the second reaction stage
(7) a phase separator
(8) the extraction stage
(9) a distillation stage
(9A) another distillation stage
(10) a water evaporator
(11) a tank for waste water
(12) a tank for end product of the process and
(12A) another tank for end product of the process.

The numerals (13) to (24.) denote the streams of different substances referred to in the examples.

In the single stage reaction process, the reaction stages (5) and (6) are combined into a single stage. Both the first and the second reaction stage may be carried out in a single reactor or in several reactors connected in series. Column reactors and/or cascades of stirrer vessels connected in series have proved to be particularly suitable for maintaining the above mentioned dwell times. The extraction stage may also be carried out in one or more extractors connected in series. Conventional counter current extraction apparatus are preferably used for this purpose.

Distillation stages (9) and (9A) consist, in the simplest case, of one distillation column designed to enable hydrophobic solvent and aniline to be substantially separated from the product of the process.

It is to be regarded as a particular advantage of the process according to the invention that the separation of hydrophobic solvent from the aniline is not necessary since the aniline content in the distillate is always below the value required for reuse, which is adjusted by the addition of fresh aniline prior to reuse. It is therefore possible to use energy saving multi-stage distillation techniques for dealing with the whole problem of distillation.

The water of condensation and the water introduced into the system with the aqueous formaldehyde solution must be removed from the system at some suitable stage in order to keep the volume of water constant. If an aminal preliminary stage (3) is carried out, this removal of water preferably takes place in the water separator (4) before the aminal is brought together with the acid catalyst. In the absence of an aminal preliminary stage, the water is preferably removed in a water evaporator (10) arranged downstream of the extraction stage (8). This water evaporator is preferably operated on the principle of flash evaporation by application of a vacuum. Removal of the water from the system could, in principle, be carried out by distillation at any other stage.

The washing water which results from the removal of traces of acid (to be described in detail below) from the organic phase or phases in the separator (7) or the extraction stage (8) and which is to be returned to the reaction mixture at some suitable point, preferably before phase separation (7) or extraction of the aqueous phase at (8) is also removed from the circulation by distillation in the evaporator stage (10).

If a preliminary aminal stage (3) is used, the introduction of aqueous formaldehyde solution into the system takes place mainly in this preliminary aminal stage although some of the formaldehyde may be added down stream of the water separator (4). Such additional input of formaldehyde is advisable in those cases in which end products with a higher proportion of tri- and higher functional polyamines are desired. The quantity of formaldehyde introduced generally corresponds to a molar ratio of aniline:formaldehyde in the aminal preliminary stage of from 1.5:1 to 25:1, preferably from 1.8:1 to 10:1.

Due to the use of a hydrophobic solvent, the process according to the invention is technically clearly superior to analogous processes not using a hydrophobic solvent, especially at low aniline/formaldehyde ratios since in these processes solid to semi-solid, technically difficult to handle products are formed even at an aniline/formaldehyde equivalent ratio below 2.5:1 when the preferred operating temperatures of up to 60° C. are employed, and the separation of the water of condensation and aqueous formaldehyde gives rise to difficulties due to the insufficient difference in densities.

When the process according to the invention is carried out without an aminal preliminary stage, introduction of the aqueous formaldehyde into the system is carried out after the solvent containing aniline has been mixed with the aqueous catalyst phase, which also contains aniline, and before the first reaction stage (5). In that case, the quantity of aqueous formaldehyde is generally calculated to provide a molar ratio of aniline/formaldehyde of from 1.5:1 to 25:1, the calculation of the molar aniline/formaldehyde ratio including both the aniline present in the solution of aniline in hydrophobic solvent which is introduced upstream of the first reactor (5) and the at least partially protonated aniline of the aqueous phase which is returned from the extractor (8) and is to be fed in at this point. High aniline/formaldehyde ratios within the broad ranges mentioned above are necessary for producing polyamines with a high diamine content. The aniline participating in the reactions is formally composed as follows:

(I) Aniline in a mixture with hydrophobic solvent as obtained from the separation in distillation stage (9) and optionally (9A). This mixture invariably contains less aniline than the mixture of aniline and hydrophobic solvent preferably used for the extraction stage (8) and for the chemical reaction in the aminal stage (3) and/or the first reaction stage (5). The difference must therefore be made up with (II) fresh aniline. In the partial stream of distillate used in the extraction stage, this addition of aniline invariably takes place upstream of the extraction stage (8). The aniline added downstream of the separator (7) and upstream of the extraction stage (8) mainly reappears in the aqueous phase from (8) and forms part of the aniline mentioned below under (III). In the partial streams used in the condensation reaction, the addition of fresh aniline preferably also takes place before the chemical reaction in (3) and (5) although the fresh aniline could in principle be added at a later stage of the reaction, for example prior to phase separation (7), but a quantity of aniline conforming to the extraction conditions must be added to the aqueous phase before entry into the extraction stage (8), at the latest after phase separation.

(III) Another contribution to the aniline taking part in the reactions, at least of the first and second acid rearrangement, is provided by the aqueous catalyst phase in circulation, which has the usual composition found in conventional extraction processes and still contains aniline and small quantities of end products of the process in addition to the catalyst and water. This aniline is formally composed of the aniline which is present in excess in the reaction and carried in the circulating system and the fresh aniline obtained from the extracting agent and exchanged for the products of the process in the extraction stage.

In the preferred embodiment in which a preliminary aminal stage is carried out, the aniline to be used in this preliminary stage is composed of (I) (distillate partial stream of aniline and hydrophobic solvent) and (II) (fresh aniline), the equivalent ratio of this aniline to the formaldehyde in the aminal stage being from 1.5:1 to 25:1, preferably from 1.8:1 to 10:1.

The reaction product of the aminal preliminary stage consists of an organic phase which, in addition to excess aniline, contains the aminal-type reaction products of aniline and formaldehyde, water which has been introduced and the water of condensation, and water soluble impurities of formaldehyde, such as methanol, formic acid, and the like as well as water soluble impurities of aniline such as cyclohexylamine, pyridine and the like. In the phase separator (4) the aqueous phase is separated and the organic phase is mixed in a first reaction stage (5) with the aqueous catalyst phase in the circulating system, which catalyst phase contains a certain amount of aniline (III) in addition to catalyst. The aniline/formaldehyde ratio in the diphasic reaction mixture is thereby increased at this stage of the reaction process and the composition of the end product is therefore influenced in the direction of an increased proportion of dinuclear products.

If there is interest in obtaining a very high yield of higher nuclear polyamines, a second preferred embodiment of the process according to the invention is carried out in the same manner as the first but with a low aniline/formaldehyde ratio within the above mentioned range prior to the aminal stage and with the additional difference that after the organic phase from the aminal preliminary stage has been mixed with the aqueous catalyst phase from the circulating system, additional formaldehyde is added at (5). Optionally, all three partial streams are mixed simultaneously at (5). Compared with the first embodiment, this embodiment enables end products with a lower diamine content to be obtained but the improved quality due to the aminal preliminary stage is preserved proportionately.

A third embodiment according to the invention, in which the aminal preliminary stage is dispensed with completely and all the formaldehyde is reacted in the first reaction stage (5) with the previously combined portion of distillate of aniline and hydrophobic solvent (I) and optionally fresh aniline (II) and aqueous circulating catalyst (III) is therefore less preferred than the above mentioned two embodiments but is still clearly superior to the known process of the prior art since it results in qualitatively improved end products, especially in the range of low diamino diphenyl methane contents (>70%).

In a fourth embodiment of the process according to the invention, which is also preferred, the procedure is analogous to that of the first embodiment except that the organic phase of the aminal preliminary stage (3) is first reacted in the first reaction stage (5) with a portion, generally less than 50%, preferably less than 15%, of the aqueous catalyst phase in circulation, preferably in the lower region of the temperature range indicated above and for a suitable residence time. The remaining quantity is added in a further stage after completion of the first and before completion of the second reaction stage (6). It is immaterial whether this remaining quantity is added at the preferred, lower temperature range of the second reaction stage (about 60° to 100° C.) or at a higher temperature. The distillation stage (10) may in this case be arranged either upstream of the separation of the aqueous phase from (8) (as illustrated) or downstream of the separation into one or both partial streams (not illustrated).

In the fifth and sixth embodiments of the process of the invention, the methods of the second and third embodiment are combined with the principle of sub-dividing the aqueous catalyst circulation adopted in the fourth embodiment.

Compared with the known art process, the first three process variations described above provide a higher 2,4'-isomer content for a comparable diaminodiphenyl methane content in the reaction products. In the second three variations, this 2,4'-isomer content may be further increased by controlled amounts within wide limits while the 2,2'-isomer content can be kept low compared with that normally obtained in products with a high 2,4'-isomer content produced by the known art processes.

The aniline is preferably added in the form of a 30 to 70% by weight, in particular a 40 to 70% by weight solution of aniline in hydrophobic solvent.

In all the above mentioned variations of the process according to the invention, the fresh aniline and the mixture of solvent and aniline which is essential to the present invention and which is obtained as distillate from the stage of distillation, may in principle be introduced into the system separately at the stages indicated but such a procedure is uneconomical and therefor less preferred.

In the case of a single stage process carried out with an aminal preliminary stage, the acid catalyst is added before or at the stage of molecular rearrangement whereas in a two-stage process it is added before or at the first rearrangement stage (5) and optionally also in the form of a partial stream after the first rearrangement stage. The catalyst is in this case used in the form of the aqueous solution of the corresponding ammonium salts obtained from the extraction stage (8) and returned to the process. This solution generally contains minor quantities of at least partially protonated MDA in addition to partially protonated aniline. The degree of protonation (percentage of all nitrogen atoms present in the form of ammonium groups) is generally from 25 to 70%, preferably from 40 to 65% in the returned aqueous phase. The concentration of at least partially protonated amines in the aqueous phase at the exit from the extractor (8) is generally from 25 to 60% by weight and at the exit from the water evaporator (10) optionally interposed into the system the percentage is from 30 to 70%. In all the embodiments described above (addition of acid at one point or at two different points), the quantity of acid generally corresponds to an equivalent ratio of nitrogen to acid at the exit from the rearrangement reactor (single stage process) or the second rearrangement reactor of from 2:1 to 20:1, preferably from 3:1 to 8:1.

When using an aminal preliminary stage, the total quantity of solvent/aniline mixture is preferably added before or at the aminal stage but with regard to the conditions stated above concerning the aniline/formaldehyde ratio. A further quantity of the mixture may in addition be supplied (i) before or at the rearrangement stage (single stage process) or (ii) before or a the first rearrangement stage (5) and/or before or at the second rearrangement stage (6) (two-stage process).

If no aminal preliminary stage is used, the stream of solvent is preferably introduced before or at the first stage (5) and in accordance with the conditions mentioned above concerning the aniline/formaldehyde ratio. An additional quantity of the mixture is optionally introduced downstream of the first stage (5) and upstream or at the second stage (6).

As a result of the fact that the process according to the invention is carried out as a diphasic process, i.e. in the presence of a hydrophobic solvent, the degree of protonation in the aqueous phase is always substantially higher than would correspond to the above mentioned equivalent ratio of amine nitrogen to acid since the major proportion of non-protonated amine is present in the solvent.

The reaction mixture leaving the rearrangement stage (single stage process) or the second rearrangement stage (6) is separated in the phase separator (7) into an aqueous phase to be transferred to the extractor (8) and an organic phase. The organic phase obtained already contains a proportion of the end product of the process and is separated, either on its own in distillation stage (9A) or together with the organic phase from extraction stage (8) in distillation column (9), into the end product of the process (distillation residue) and an aniline-containing solution (distillate). The end products of the process present in the organic phase from (7) always contain a higher proportion of ortho-isomers than the end products left in the aqueous phase. Separate working up by distillation is therefore to be carried out if there is interest in obtaining end products containing a relatively high proportion of ortho-isomers. The ratio by weight of end products of the process present in the organic phase from (7) to the end products of the process present in the aqueous phase from (7) is generally from 0.2:1 to 3:1 and depends to a great extent on the quantities of water, acid and solvent present in the reaction mixture which is introduced into the phase separator (7).

The aqueous phase leaving the phase separator (7) is extracted with aniline-containing hydrophobic solvent in extraction stage (8). The same solvent is preferably used for this purpose as the one already added to the reaction mixture at the beginning of or during the reaction. The mixture of solvent and aniline used for extraction generally has an aniline content of from 30 to 70%, preferably from 40 to 60%.

The ratio weight by weight of organic phase to aqueous phase at the entrance to the extraction stage (8) is from 0.5:1 to 3:1, preferably from 0.7:1 to 2:1. The extraction stage generally consists of one or more counter flow extractors connected in series. The extraction is preferably carried out within the temperature range of from 60° to 100° C., in particular from 85° to 98° C.

The aqueous phase leaving the extraction stage (8) contains the catalyst and is returned to the beginning of the process, as already described. The organic phase leaving the extraction stage (8) is separated, either together with the organic phase obtained from the phase separator (7) or separately, in distillation stage (9), into end product of the process (distillation residue) and aniline-containing solvent (distillate). The distillate obtained is partly used again for extraction and partly returned to the beginning of the process after the addition of fresh aniline to restore it to the original aniline content.

According to a particular variation of the procedure for working up the reaction mixtures according to this invention, the organic phases leaving the phase separator (7) and/or the extraction stage (8) are washed with water (not shown) to remove traces of acid carried in before they are worked up by distillation. The water used for washing may be that obtained, for example, from (4) or (10). After it has been used for washing, preferably by a process of multi-stage counterflow extraction, the water is returned to the reaction mixture together with the removed traces of acid at any stage of the process prior to the extraction stage (8). It is particularly preferred (i) to feed the wash water back into the reaction mixture after the second rearrangement (6) and before entry into the phase separator (7) or (ii) to return the wash water to the aqueous phase after it has left the phase separator (7) and before its entry into the extraction stage (8). Most preferably, a quantity of water greater than that required for maintaining a constant volume of water in circulation is removed by distillation at (10) from the aqueous phase leaving the extraction stage (8). This excess water over and above that required for keeping the volume constant is then used as washing water. Even when no washing with water is carried out, it is frequently advantageous to return such a quantity of water removed at (10) directly into the reaction mixture at the stated points (i) or (ii).

The ratio by weight of water put into the process or directly introduced into the reaction mixture to the quantity of organic phase present at the point where the water is introduced is generally from 1:5 to 1:50, preferably from 1:8 to 1:20.

The invention is further illustrated but is not intended to be limited by the following examples in which all parts and percentages are by weight unless otherwise specified.

EXAMPLES

Example 1

(FIG. 1)

A 30% aqueous formaldehyde solution (substance stream (13)) is reacted with an aniline-xylene mixture (substance stream (14)) at 40° C. in a reactor (3) composed of two stirrer vessels arranged in series.

(13) 0.5 kg/h formaldehyde, 1.16 kg/h water.
(14) 3.10 kg/h aniline, 2.60 kg/h ortho-xylene.

In the following separator (4), the lower, aqueous phase is separated off as waste water at 40° C.

The upper, organic phase is transferred to a second reactor (5) composed of three stirrer vessels, where it is mixed with the substance stream (15).

(15) 0.1 kg/h polyarylamine, 1.83 kg/h aniline, 0.44 kg/h hydrogen chloride, 2.64 kg/h water.

The temperature in the three vessels of the reactor (5) which are measured and controlled are 30° C., 40° C. and 60° C.

In another reactor (6) also composed of three stirrer vessels, the reaction mixture passes through the temperature stages of 100° C., 130° C. and 140° C., which are adjusted by heating the reaction mixture at its intrinsic pressure that becomes established during the reaction.

After the reaction mixture has cooled to 95° C. and the pressure has been released to normal pressure and after the addition of HCl-washing water from the extraction stage (not shown) which is situated downstream of extraction stage (8) (substance stream (22)), the organic phase (substance stream 16)) and the aqueous phase (substance stream (17)) are separated from one another in the phase separator (7).

(16) 1.09 kg/h polyarylamine, 1.18 kg/h aniline, 2.60 kg/h ortho-xylene.
(17) 2.09 kg/h polyarylamine, 0.70 kg/h aniline, 0.45 kg/h hydrochloric acid, 4.04 kg/h water.

The aqueous phase is then continuously extracted in counter current to an aniline-xylene mixture (substance stream (18)) in the extraction column (8).

(18) 3.92 kg/h aniline, 3.28 kg/h ortho-xylene.

The extracted aqueous phase from (8) (substance stream (19)) is concentrated in distillation stage (10) with removal of water, and is subsequently returned to the reactor (5) as substance stream (15).

The resulting organic phase from (8) (substance stream (20)) is combined with the organic phase from the separator (7) (substance stream (16)) and extracted in another extraction column operating as a 3-5 stage extractor (not shown) with the distillate from distillation stage (10) (not shown) which consists substantially of 1,38 kg/h water.

(20) 1.99 kg/h polyarylamine. 2.81 kg/h aniline, 3.27 kg/h ortho-xylene.

In the washing stage (not shown), the HCl content of the substance stream (16) and (20), which is approximately 0.2 to 0.3% by weight, is reduced to <0.01% by weight under the conditions indicated.

The HCl-containing washing water (about 1.5 kg/h) is recycled into the reaction mixture.$^x$ $^x$ The extracted of stream (20) which is no essential process step has not been shown in the drawings.

After removal of residual traces of acid by neutralization with excess sodium hydroxide solution and removal of the resulting sodium chloride and of unused sodium hydroxide solution, the organic phase (16) and (20) leaving the washing column is separated by distillation in distillation stage (9) into a distillate (substance stream (21)) and a distillation residue (substance stream (22)) consisting of polyarylamine.

(21) 4.23 kg/h aniline, 5.86 kg/h ortho-xylene, (<0.5% by weight polyarylamine).
(22) 3.00 kg/h polyarylamine, (<0.1% by weight aniline).

After the addition of fresh aniline (substance stream (23)) from the storage tank (2) to the substance stream (21), the resulting mixture of aniline and xylene (substance stream (24)) is sub-divided quantitatively and reused as substance streams (14) and (18).

The distillation residue (22) from distillation stage (9) has the following composition:
67% by weight diamino diphenyl methanes,
33% by weight multinuclear polyarylamines.

The dinuclear polyarylamine fraction had the following composition:
0.5% by weight 2,2'-diamino diphenyl methane,
11.9% by weight 2,4'-diamino diphenyl methane,
87.6% by weight 4,4'-diamino diphenyl methane.

Example 2

(FIG. 1)

The procedure is analogous to that of Example 1, but with this difference that in addition to the supply of formaldehyde into the reactor (3) (substance stream (13)), a further quantity of formaldehyde is introduced into the reactor (5) (substance stream 13'=0.66 kg/h of 30% formaldehyde).

A corresponding quantity of water (about 0.6 kg/h) is accordingly removed from the increased quantity of distillate from evaporation stage (10) in addition to the water separated off in the separator (4) in order to keep the amount of water in the catalyst circulation constant.

(13) 0.5 kg/h formaldehyde, 1.16 kg/h water.
(14) 3.10 kg/h aniline, 2.60 kg/h ortho-xylene.
(15) 0.1 kg/h polyarylamine, 1.83 kg/h aniline, 0.44 kg/h hydrochloric acid, 2.69 kg/h water.
(13') 0.2 kg/h formaldehyde, 0.46 kg/h water.
(16) 1.11 kg/h polyarylamine, 0.83 kg/h aniline, 2.58 kg/h ortho-xylene.
(17) 2.9 kg/h polyarylamine, 0.4 kg/h aniline, 0.46 kg/h hydrochloric acid, 4.05 kg/h water.
(18) 5.58 kg/h aniline, 4.65 kg/h ortho-xylene.
(19) 0.1 kg/h polyarylamine, 1.82 kg/h aniline, 0.44 kg/h hydrochloric acid, 3.81 kg/h water.
(20) 2.86 kg/h polyarylamine, 4.16 kg/h aniline, 4.65 kg/h ortho-xylene.
(21) 3.95 kg/h polyarylamine, 4.92 kg/h aniline, 7.23 kg/h ortho-xylene.
(22) 3.95 kg/h polyarylamine.
(23) 3.66 kg/h aniline.

The distillation residue (22) from distillation stage (9) has the following composition:
52% by weight diamino diphenyl methane.
48% by weight multinuclear polyarylamine.

The dinuclear polyamine fraction has the following composition:
0.6% by weight 2,2'-diamino diphenyl methane,
10.6% by weight 2,4'-diamino diphenyl methane,
88.8% by weight 4,4'-diamino diphenyl methane.

Example 3

(FIG. 1)

The procedure is analogous to that of Example 1 and is carried out in the same experimental plant with the same experimental arrangement but with the following substance streams:

(13) 0.24 kg/h formaldehyde, 0.56 kg/h water.
(14) 5.74 kg/h aniline, 4.40 kg/h ortho-xylene.
(15) 0.23 kg/h polyarylamine, 3.77 kg/h aniline, 0.65 kg/h hydrochloric acid, 3.22 kg/h water.
(16) 0.54 kg/h polyarylamine, 5.23 kg/h aniline, 4.40 kg/h ortho-xylene.
(17) 1.04 kg/h polyarylamine, 3.01 kg/h aniline, 0.65 kg/h hydrochloric acid, 3.22 kg/h water.

(18) 8.26 kg/h aniline, 6.30 kg/h ortho-xylene.
(20) 0.81 kg/h polyarylamine (1,15 kg/h water from 10)), 7.50 kg/h aniline, 6.29 kg/h ortho-xylene.
(21) 12.73 kg/h aniline, 10.74 kg/h ortho-xylene.
(22) 1.35 kg/h polyarylamine.
(23) 1.27 kg/h aniline.

The distillation residue (22) of distillation stage (9) has the following composition:
  92% by weight diamino diphenyl methanes,
  8% by weight multinuclear polyarylamines.

The dinuclear polyarylamine fraction has the following composition:
  1.6% by weight 2,2'-diamino diphenyl methane,
  21.4% by weight 2,4'-diamino diphenyl methane,
  77.0% by weight 4,4'-diamino diphenyl methane.

Example 4

(FIG. 2)

This example corresponds to Example 3 except that the organic substance stream (20) is worked up into a polyarylamine partial product-1 (substance stream (22')) in distillation stage (9) and the organic substance stream (16) is worked up into a polyarylamine partial product-2 (substance stream (22'')) in a separate distillation stage (9A).

The distillates are combined to form substance stream (21).

The distillation residues have the following composition:
  Polyarylamine-1 (0.810 kg/h):
    91.3% by weight diamino diphenyl methanes
    8.7% by weight multinuclear polyarylamines The dinuclear polyarylamine fraction has the following composition:
  0.7% by weight 2,2'-diamino diphenyl methane,
  17.1% by weight 2,4'-diamino diphenyl methane,
  82.2% by weight 4,4'-diamino diphenyl methane.
  Polyarylamine-2 (0.540 kg/h):
    92.7% by weight diamino diphenyl methanes,
    7.3% by weight multinuclear polyarylamines.

The dinuclear polyarylamine fraction has the following composition:
  3.1% by weight 2,2'-diamino diphenyl methane,
  29.2% by weight 2,4'-diamino diphenyl methane,
  67.7% by weight 4,4'-diamino diphenyl methane.

Example 5

(FIG. 1)

The procedure is analogous to that of Example 3 except that the substance stream (13) and (14) bypass the reactor (3) and the separator (4) and flow directly into reactor (5) where they are mixed with substance stream (15) to be reacted therewith. A correspondingly larger quantity of water (II) must therefore be distilled off in distillation stage (10) (no water removed at (4)) by comparison with Example 3, in which formaldehyde-water and water of condensation are separated in the separator (4).

Distillation residue (22) of distillation stage (9) has the following composition:
  89% by weight diamino diphenyl methanes,
  11% by weight multinuclear polyarylamines.

The dinuclear polyarylamine fraction has the following composition:
  1.5% by weight 2,2'-diamino diphenyl methane,
  20.1% by weight 2,4'-diamino diphenyl methane,
  78.4% by weight 4,4'-diamino diphenyl methane.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of multinuclear aromatic polyamines by the reaction of aniline with formaldehyde in the presence of water and acid catalysts in a single stage or two-stage reaction within the temperature range of from 0°–180° C., optionally preceded by an aminal preliminary stage in which the formation of N,N'-disubstituted aminal takes place in the absence of acid catalyst, which aminal is then converted into the desired end product in one or more stages in the presence of acid catalyst within the temperature range of from 0° to 180° C., working up of the resulting reaction mixture by extraction with an aniline-containing hydrophobic solvent, separation by distillation of the resulting organic phase into (i) a distillate consisting of aniline-containing solvent, which distillate is used again for extraction, optionally after the addition of fresh aniline, and (ii) a distillation residue consisting substantially of end product of the process and return of the aqueous phase obtained from the extraction process and containing acid catalyst, with reuse of the catalyst contained in the aqueous phase and removal of the water of condensation formed in the condensation reaction and of the water introduced into the system with the aqueous solution of formaldehyde in a water separator placed downstream of the aminal preliminary stage and upstream of the first reaction stage and/or in an evaporator placed downstream of the extraction stage and upstream of the first reaction stage, characterized in that (a) the formaldehyde which is put into the process in the form of an aqueous solution is mixed with and thereby reacted with aniline-containing hydrophobic solvent in an aminal preliminary stage and/or with an aniline-containing hydrophobic solvent and recycled aqueous phase containing the catalyst in the form of amine salts in the first reaction stage (b) after termination of the reaction, the diphasic reaction mixture obtained is separated into an aqueous phase and an organic phase in a phase separator arranged upstream of the extraction stage (c) the organic phase obtained in the phase separator is separated by distillation, either separately or together with the organic phase leaving the extraction stage, into (i) a distillate consisting of aniline-containing solvent or two distillates consisting of aniline-containing solvent and (ii) one or two distillation residues consisting substantially of end product of the process, and (d) two partial streams are produced from the distillate according to (c) or the distillates according to (c), which two partial streams may be identical with the two distillates according to (c), one of the partial streams is mixed with the aqueous formaldehyde in the aminal preliminary stage or, in the absence of an aminal preliminary stage, it is mixed in the first reaction stage with the aqueous formaldehyde and the aqueous phase containing the acid catalyst, and the other partial stream is used in the extraction stage for the extraction of the end product of the process from the aqueous phase of the reaction mixture.

2. The process according to claim 1, characterized in that a quantity of water greater than that required for maintaining a constant volume of water in circulation is removed by distillation from the aqueous phase leaving the extraction stage, and the quantity of water exceeding that required for keeping the water volume constant is returned to the circulation at any desired point downstream of the last reaction stage and upstream of the extraction stage.

3. The process according to claim 1, characterized in that the aqueous phase containing the acid catalyst is separated into two partial streams after it has left the extraction stage and before it is reused, and one partial stream is added to the first reaction stage and the other partial stream is added to the reaction mixture after termination of the first reaction stage and before termination of the second reaction stage.

4. A process for the preparation of multinuclear aromatic polyamines comprising
(A) reacting aniline and formaldehyde in the presence of water, hydrophobic solvent and acid catalysts in one or more stages, to produce a two-phase condensation mixture containing said aromatic polyamines,
(B) separating said condensation mixture into an aqueous phase and an organic phase,
(C) extracting said aqueous phase with a hydrophobic solvent containing aniline to produce a solvent phase and a second aqueous phase which contains the acid catalyst,
(D) subjecting said organic phase and said solvent phase to distillation to produce (i) a distillate containing said hydrophobic solvent and aniline, and
(ii) a distillation residue which contains said aromatic polyamines,
(E) returning a portion of said distillate to step (A),
(F) returning the remaining portion of said distillate to step (C), and
(G) returning said second aqueous phase to step (A).

5. The process of claim 4 wherein step (A) comprises
(Ai) condensing aniline with formaldehyde in the presence of a hydrophobic solvent and in the absence of an acid catalyst to produce a precondensate mixture containing the corresponding N,N'-disubstituted aminals,
(Aii) removing substantially all the water from said precondensate mixture,
(Aiii) mixing the resultant water-free mixture with an aqueous solution containing acid catalyst to produce a two-phase mixture, and
(Aiv) subjecting said two-phase mixture to a rearrangement reaction in one or more stages thereby producing an aqueous condensation mixture containing said aromatic polyamines.

6. The process of claim 5, wherein step (E) comprises returning a portion of said distillate to step (Ai).

7. The process of claim 6, wherein step (G) comprises returning said second aqueous phase to step (Aiii).

8. The process of claim 4, wherein step (D) comprises separately distilling said organic phase and said solvent phase.

9. The process of claim 4, wherein step (D) comprises combining said organic phase and said solvent phase and subjecting the resultant mixture to distillation.

* * * * *